United States Patent [19]

Drauz et al.

[11] Patent Number: 4,825,011

[45] Date of Patent: Apr. 25, 1989

[54] METHOD OF PREPARING SUBSTITUTED DIHYDROXY-BENZENES

[75] Inventors: Karl-Heinz Drauz, Freigericht; Axel Kleeman, Mühlheim; Günter Prescher; Gebhard Ritter, both of Hanau, all of Fed. Rep. of Germany

[73] Assignee: Degussa AG, Fed. Rep. of Germany

[21] Appl. No.: 128,605

[22] Filed: Dec. 4, 1987

[30] Foreign Application Priority Data

Dec. 18, 1986 [DE] Fed. Rep. of Germany ....... 3643206

[51] Int. Cl.$^4$ .................... C07C 37/60; C07C 41/00
[52] U.S. Cl. .................................. 568/771; 568/650; 568/651; 568/803
[58] Field of Search ............... 568/771, 803, 650, 651

[56] References Cited

U.S. PATENT DOCUMENTS

| 3,943,179 | 3/1976 | Bost et al. | 568/771 |
| 4,533,766 | 8/1985 | Drauz et al. | 568/771 |
| 4,551,562 | 11/1985 | Drauz et al. | 568/771 |
| 4,590,305 | 5/1986 | Drauz et al. | 568/771 |
| 4,618,730 | 10/1986 | Drauz et al. | 568/771 |
| 4,628,126 | 12/1986 | Drauz et al. | 568/771 |

Primary Examiner—Werren B. Lone
Attorney, Agent, or Firm—Cushman, Darby & Cushman

[57] ABSTRACT

The nuclear hydroxylation of substituted phenols is performed by using aqueous hydrogen peroxide in the presence of sulfur dioxide or selenium dioxide as catalyst in a simple manner with very good space-time yields and good product yields.

9 Claims, No Drawings

METHOD OF PREPARING SUBSTITUTED DIHYDROXY-BENZENES

The present invention relates to the preparation of substituted dihydroxybenzenes by hydroxylating substituted phenols with aqueous hydrogen peroxide.

BACKGROUND OF THE INVENTION

Dihydroxybenzenes are used in the manufacture of dyes in the plastics industry, photographic industry and agricultural pesticide industry.

German Patent Specification No. 20 64 497 discloses a method of nuclear hydroxylation of aromatic compounds, especially of phenol, with hydrogen peroxide in the presence of a strong acid. In this method, the reaction medium should not contain more that 20% by weight water initially, preferably less than 10% by weight water.

The pH of the strong acids is indicated to be under −0.1, preferably under −1. Sulfuric acid and perchloric acid appear to be preferred strong acids.

However, this method is criticized in by the applicant of German Patent Specification DE-PS No. 20 64 497 himself in his later German Patent Specification DE-PS No. 26 58 545. Thus, the yields of hydroxylation products are said to be "excellent" with the simultaneous usage of the strong acids and of complexing agents for metals like pyrophosphoric acid; however, the degree of conversion of the aromatic compound is under 30%. In practice, conversions of 4 to 10% were not exceeded.

This results in a limitation on the productivity of the apparatus and the recovery of a significant volume of unused raw material.

As high a reaction speed as possible would be desirable. This would depend, at a given temperature and amount of water, on the type and amount of the acid used. However, it would be desirable, regardless of the type of acid, to increase the reaction speed without increasing the amount of acid, since the latter would be lost by being washed out and, moreover, the corrosion due to the strong acid is undesirable.

Thus, DE-PS No. 26 58 545 suggests, as an improvement of the above-mentioned method, in addition to the catalysts and stabilizers cited in it, the addition of aromatic aldehydes such as benzaldehyde to the reaction mixture. The hydroxylation of phenol and substituted phenols with hydrogen peroxide thus occurs in the presence of strong acids, metal complexing agents and aromatic aldehydes.

Instead of two components which influence the reaction, three must therefore be used. These components must not only be separated out of the reaction mixture and are lost as non-recoverable but, in addition, the "aromatic aldehyde" component is subject to an oxidation with hydrogen peroxide, which leads to the risk of contamination of the final product.

However, higher yields of approximately 70–76% and in two instances over 80% are also only obtained here if phenol/hydrogen peroxide ratios of 20:1 and hydrogen peroxide of approximately 85% concentration are used. However, in these instances "a significant volume of initial material must be recovered", as in DE-PS No. 20 64 497, which necessitates recovery systems. Even the reactors themselves must be designed to be correspondingly large.

Since the yield of catechol and hydroquinone drops considerably in the method of DE-PS No. 20 64 497 as the ratio of phenol to hydrogen peroxide decreases—at a ratio of 10:1 it is 60% and at a ratio of 5:1 at 47%, cf. example 7—the presence of a large excess of phenol appears to be a necessity when performing the hydroxylation with strong acid, quite apart from the fact that the strong acids such as sulfuric acid and perchloric acid named in DE-PS No. 20 64 497 only had a weak catalytic action. The yields were even worse in the case of substituted phenols.

The assumption was therefore made that the catalytic action of the strong acids could be improved by using water-free solutions of hydrogen peroxide—cf. German Patent Specifications DE-PS No. 24 10 742 and DE-OS No. 24 10 758; however, the presence of phosphorus compounds as complexing agents was also considered to be essential here. In addition, it was pointed out that the reaction occurred the fastest at high concentrations of acid. The question of corrosion by strong acids was therefore also not solved here.

A considerable advance over the mentioned methods is represented by the methods of German Patent Specifications DE-PS No. 33 08 737 (corresponding to U.S. Pat. No. 4,618,730); DE-PS No. 33 08 769 (corresponding to U.S. Pat. No. 4,533,766); DE-PS No. 33 08 763 (corresponding to U.S. Pat. No. 4,590,305) and DE-PS No. 33 08 726 (corresponding to U.S. Pat. No. 4,551,562) in which the hydroxylation of phenol or its derviatives was performed by organic solutions of hydrogen peroxide in the presence of sulfur dioxide or selenium dioxide.

The undesirable consequences of using strong acids, such as corrosion, did not occur in these methods, nor was it necessary to use additional compounds such as aldehydes or even complexing agents such as phosphorus derivatives in order to increase the activity.

Although the catalysts were used in very small amounts, the reaction speed was high; very advantageous space-time yields and very good yields were obtained. Due to their very small concentration, sulfur dioxide and selenium dioxide also require no special separation methods.

According to the state of the art, therefore, only the usage of water-free solutions of hydrogen peroxide appeared at first to result in better conversions and yields. However, when strong acids were used as catalyst, there was still the problem of separating them out as well as the occurrence of corrosion.

The usage of sulfur dioxide or selenium dioxide made a considerable advance here. However, even these methods required water-free solutions of hydrogen peroxide which were not supposed to contain more than 1% by weight, preferably less than 0.5%, by weight water. This method of operation also requires additional systems for separating and recycling the organic solvent.

SUMMARY OF THE INVENTION

The object of the present invention is to carry out the hydroxylation of substituted phenols with sulfur dioxide or selenium dioxide in an improved manner.

In accordance with the present invention, it has been found that this can be achieved if the hydroxylation of substituted phenols is performed in the presence of sulfur dioxide or selenium dioxide as catalyst with aqueous hydrogen peroxide solutions. The ratio of the substituted phenols to hydrogen peroxide is 5 to 25:1, preferably 10 to 16:1 (in moles).

Hydrogen peroxide is added in commercial solutions in the approximate concentrations; the conversion is performed with 30–85% by weight solutions, preferably 70–85% by weight solutions. The sulfur dioxide added is of a purity of 99.75% by weight.

The catalysts, sulfur dioxide or selenium dioxide, are used in amounts of 0.0001 to 0.04 mole for each mole of hydrogen peroxide.

Sulfur dioxide is added in liquid or in gaseous form from commercial steel bottles or as solutions in e.g. alkyl esters, alkanes such as e.g. cyclohexane or in the substituted phenols.

SeO$_2$ is added in p.a. form.

The conversions are performed at temperatures of 20°–160° C. The pressure is not important; in general, the process is carried out at atmospheric pressure.

Examples of substituted phenols which can be used as raw materials include: Alkyl derivatives of phenol such as the cresols, ethyl or butyl phenols and, from the latter, especially o- and p-tert. butyl phenol particularly p-tert. butyl phenol. Phenols substituted in the p-position were generally quite suitable for the method of the invention. Moreover, alkoxy phenols such as e.g. anisole or aryl phenols such as e.g. 4-hydroxydiphenyl also proved to be advantageous starting materials, as well as halogenated phenols such as e.g. o- and p-chlorophenol and phenylethyl and phenylisopropylether. p-tert.-butyl phenol, anisole and p-cresol were preferred. The starting materials can be introduced both as melts or in suitable inert organic solvents such as aromatic hydrocarbons, e.g. benzene/toluene, cycloaliphatic hydrocarbons such as e.g. cyclohexane, aromatic and aliphatic esters such as e.g. propyl acetate or chlorinated hydrocarbons such as e.g. chloroform or carbon tetrachloride.

The method can be performed either discontinuously or continuously. The substituted phenol recycled in the method of the invention requires no particular treatment.

The technical advance of the method of the invention is to be found in its simplicity—instead of organic hydrogen peroxide solutions in which the organic solvent must be separated out, aqueous hydrogen peroxide can be used directly. In addition, the usage of sulfur dioxide or selenium dioxide in extremely small amounts avoids the problems which occur when strong acids are used, such as an expensive procedures to separate these catalysts and corrosion. Also, the contamination of waste water by salts derived from neutralization of the acids is eliminated.

In addition, activators are not necessary for a sufficient reaction speed in the case of sulfur dioxide and selenium dioxide, and the addition of stabilizers is not necessary. This avoids additional procedures and, given the sensitivity to oxygen of the most effective activators, the contamination of the final product by oxidation products of the activators. Moreover, the high reaction speed results in an increased space-time yield.

In addition to the simplified technical performance, the process of the present invention is advantageous because the conversion of hydrogen peroxide is high and the space-time yield is higher than with organic hydrogen peroxide solutions. Moreover, the yield of hydroxybenzenes is at least as high as in the previously-known methods.

DETAILED DESCRIPTION OF PREFFERED EMBODIMENTS

The invention is further illustrated in the following examples. In these examples, the compositions of the products were determined by gas-liquid chromatography (GLC). The experiments were carried out under a nitrogen atmosphere, although no changes in the results were observed in the presence of air.

EXAMPLE 1

75 g (0.5 mole) p-tert.-butyl phenol are heated to 102° C. and 100 mg (1.56 mmole) gaseous sulfur dioxide is dissolved therein. Then, 151 g (0.031 mole) 70% by weight hydrogen peroxide is added to this mixture. The temperature in the reaction solution rises thereafter to 128° C.

After the exothermal reaction dies down, a hydrogen peroxide conversion of 99% is determined after 10 minutes. The reaction mixture then contains 4.2 g 4-tert.-butyl catechol, which corresponds to a yield of 81.5% in relation to the hydrogen peroxide added.

EXAMPLE 2

75 g (0.5 mole) p-tert.-butyl phenol are heated to 102° C. and it is compounded with 50 mg (0.78 mmole) sulfur dioxide. Then, 0.8 g (20 mmole) 85% by weight hydrogen peroxide is added to this mixture. The temperature in the reaction solution rises thereafter to 118° C. After the exothermal reaction dies down, a hydrogen peroxide conversion of 99% is determined after 10 minutes. The reaction mixture then contains 2.77 g 4-tert.-butyl catechol, which corresponds to a yield of 83.3% in relation to the hydrogen peroxide added.

EXAMPLE 3

73 g (0.5 mole) p-tert. butyl phenol are heated to 103° C. 0.4 g of a 60% solution by weight of sulfur dioxide in acetic acid n-propylester and subsequently 1.51 g (0.031 mole) 70% by weight hydrogen peroxide are added to the agitated melt. The temperature in the reaction mixture rises thereafter to 131° C. After the exotherm dies down, a hydrogen peroxide conversion of 99% is determined after 10 minutes. The reaction mixture then contains 4.11 g 4-tert.-butyl catechol, which corresponds to a yield of 80% in relation to the hydrogen peroxide used.

EXAMPLE 4

54 g (0.5 mole) anisole are heated to 120° C. and this solution is compounded with 50 mg (0.78 mmole) sulfur dioxide. Then, 1.18 g (0.029 mole) 84.4% by weight hydrogen peroxide is added to this mixture. The temperature in the reaction solution rises thereafter to 138° C. After the exotherm dies down, a hydrogen peroxide conversion of 98% is determined after 10 minutes. The reaction mixture then contains 1.88 g (0.015 mole) catechol monomethylether and 0.76 g (6 mmoles) hydroquinone monomethylether, which corresponds to a total yield of 73.3% in relation to the hydrogen peroxide used.

EXAMPLE 5

54 (0.5 mole) p-cresol is heated to 105° C. and this solution is compounded with 50 mg (0.78 mmole) sulfur dioxide. Then, 1.51 g (0.031 moles) 70% by weight hydrogen peroxide is added to this mixture. The temperature in the reaction solution rises thereafter to 135°

C. After the exotherm dies down, a hydrogen peroxide conversion of 99% is determined after 10 minutes. The reaction mixture then contains 2.77 g 4-methyl catechol and 0.31 g 4-methyl resorcinol, which corresponds to a total yield of dihydroxbenzenes of 80.1% in relation to the hydrogen peroxide added.

What is claimed is:

1. In a method of preparing a substituted dihydroxybenzene or a substituted dihydroxybenzene monoalkyl ether by nuclear hydroxylation of a substituted phenol selected from the group consisting of phenols and phenyl alkyl ethers with hydrogen peroxide;

the improvement which comprises forming a mixture which consists essentially of said substituted phenol, aqueous hydrogen peroxide and a catalyst selected from the group consisting of sulfur dioxide and selenium dioxide, and reacting the hydrogen peroxide with said substituted phenol.

2. A method according to claim 1 in which the conversion is performed with an aqueous solution which contains 70–85% by weight hydrogen peroxide.

3. A method as set forth in claim 2 in which the conversion is performed with an aqueous solution which contains 30–85% by weight hydrogen peroxide.

4. A method as set forth in any one of claims 2, 3 and 1 in which the phenol is a member of the group consisting of alkyl phenols, alkoxy phenols, aryl phenols and halogenated phenols.

5. A method as set forth in claim 4 in which the phenol is a member of the group consisting of 4-alkyl phenols, 4-alkoxy phenols, 4-aryl phenols and 4-halogenated phenols.

6. A method as set forth in claim 4 in which the phenol is selected from the group consisting of p-tert butyl phenol, anisole and p-cresol.

7. A method set forth in any one of claims 2, 3 and 1 in which the proportion of sulfur dioxide or selenium dioxide is 0.0001 to 0.04 mole for each mole of hydrogen peroxide.

8. A method as set forth in any one of claims 2, 3 and 1 in which the molar ratio of substituted phenol to hydrogen peroxide is in the range 5:1 to 25:1.

9. A method as set forth in claim 8 in which the molar ratio of substituted phenol to hydrogen peroxide is in the range 10:1 to 16:1.

* * * * *